(12) United States Patent
Sun et al.

(10) Patent No.: US 9,144,479 B2
(45) Date of Patent: Sep. 29, 2015

(54) LIGHT CURING SYSTEM AND METHOD

(75) Inventors: Benjamin J. Sun, York, PA (US);
Andrew Lichkus, York, PA (US); Scott Shaffer, Jacobus, PA (US)

(73) Assignee: DENTSPLY International Inc., York, PA (US)

( * ) Notice: Subject to any disclaimer, the term of this patent is extended or adjusted under 35 U.S.C. 154(b) by 170 days.

(21) Appl. No.: 12/460,298

(22) Filed: Jul. 16, 2009

(65) Prior Publication Data

US 2009/0278285 A1 Nov. 12, 2009

Related U.S. Application Data

(63) Continuation of application No. 11/395,387, filed on Mar. 31, 2006, now abandoned, which is a continuation-in-part of application No. 10/106,741, filed on Mar. 26, 2002, now abandoned, which is a continuation-in-part of application No. 09/682,440, filed on Sep. 4, 2001, now Pat. No. 6,592,369, which is a continuation-in-part of application No. 09/670,364, filed on Sep. 26, 2000, now abandoned.

(60) Provisional application No. 60/237,523, filed on Oct. 4, 2000.

(51) Int. Cl.
*A61C 13/15* (2006.01)
*A61C 13/00* (2006.01)

(52) U.S. Cl.
CPC ............ *A61C 19/003* (2013.01); *A61C 13/0003* (2013.01)

(58) Field of Classification Search
CPC ...................................................... A61C 19/003
USPC ................................................ 264/496, 297.7
See application file for complete search history.

(56) References Cited

U.S. PATENT DOCUMENTS

| | | | | |
|---|---|---|---|---|
| 4,468,202 A * | 8/1984 | Cohen | ........................... | 433/214 |
| 5,135,686 A * | 8/1992 | Masuhara et al. | ............. | 264/406 |
| 5,922,605 A * | 7/1999 | Feurstein et al. | ................ | 436/55 |
| 6,380,314 B1 * | 4/2002 | Soane et al. | ................... | 525/242 |
| 2002/0117393 A1* | 8/2002 | Sun et al. | ................... | 204/157.15 |

* cited by examiner

*Primary Examiner* — Larry Thrower
(74) *Attorney, Agent, or Firm* — David A. Zdurne; Douglas J. Hura; Leana Levin

(57) ABSTRACT

A method for light-curing polymerizable materials to form a dental device is provided. A light-curing apparatus having at least one integrated lighting and heating source, a curing volume, and a temperature controller, preferably a fan, is used in the method. The light source and temperature controller are used to heat a first polymerizable material to temperatures within a first temperature range. A second polymerizable material is applied on or adjacent to the first polymerizable material. The light source and temperature controller are used to heat the second polymerizable material to temperatures within a second temperature range. The first temperature range has a first midpoint and the second temperature range has a second midpoint. The first midpoint temperature is at least 10° C. apart from the second midpoint temperature. The system is particularly suitable for making dental devices such as full dentures, removable partial dentures, relines of full and partial dentures, nightguards, and occlusal splints.

20 Claims, 1 Drawing Sheet

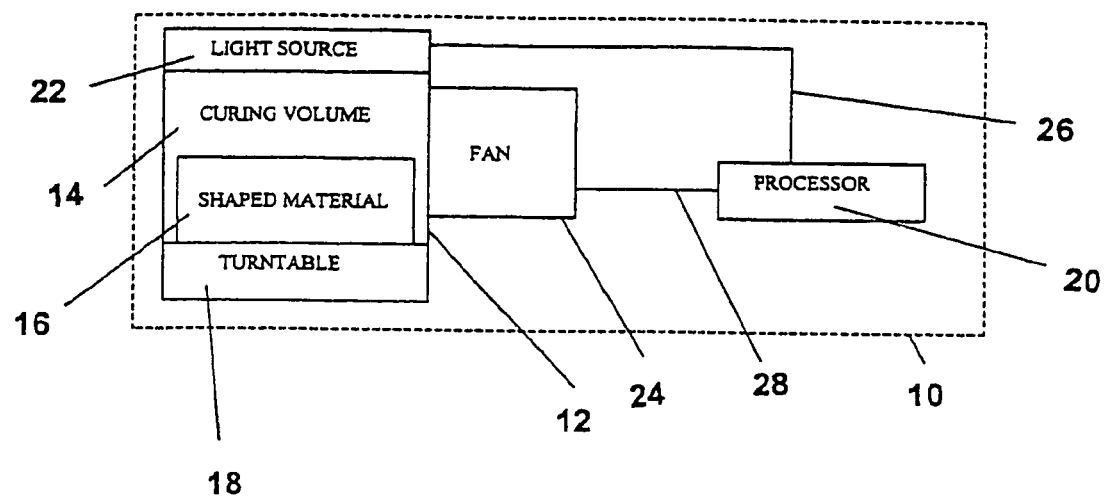

LIGHT CURING SYSTEM AND METHOD

CROSS-REFERENCE TO RELATED APPLICATIONS

This application is a continuation of U.S. patent application Ser. No. 11/395,387 filed Mar. 31, 2006 now abandoned which is a continuation-in-part of U.S. patent application Ser. No. 10/106,741 filed Mar. 26, 2002 now abandoned, which is a continuation-in-part of U.S. patent application Ser. No. 09/682,440 filed Sep. 4, 2001, now U.S. Pat. No. 6,592,369, which is a continuation-in-part of U.S. patent application Ser. No. 09/670,364 filed Sep. 26, 2000, now abandoned, further claiming the benefit of U.S. Provisional Patent Application Ser. No. 60/237,523 filed Oct. 4, 2000. The disclosures of the foregoing applications are incorporated herein by reference in their entirety.

BACKGROUND OF THE INVENTION

1. Field of the Invention

The invention relates generally to a light-curing system and method. More specifically, the system provides controlled heating of at least two different polymerizable materials within a chamber at two different temperatures. A single source provides the necessary curing light and heat to achieve polymerization of both materials. The first polymerizable material is heated to temperatures within a first temperature range, and the second polymerizable material is heated to temperatures within a second temperature range. The system is particularly suitable for making dental devices such as full dentures, removable partial dentures, relines of full and partial dentures, nightguards, occlusal splints, and the like.

2. Brief Description of the Related Art

Various light-curing systems are known in the dental arts for making dental products. For example, Masuhara et al., U.S. Pat. No. 5,135,686 ("the '686 Patent") discloses a method for curing light-polymerizable objects by placing the objects on a conveyor belt, which transports the objects through a curing apparatus. The object is conveyed to a first station, where it irradiated with visible light from a first source having relatively low radiation intensity. Moving forward, the object enters a second station, where it is irradiated with visible light from a second light source having relatively high radiation intensity. The objective of the method in the '686 Patent is to control the rate of polymerization so that the object can be fully and uniformly cured. The flux density of the irradiating light needs to be controlled in order that the object does not cure too quickly according to the '686 Patent. In one embodiment, a mixture of light-curing resins was placed in a mold and a tooth specimen was embedded in the resin—the resulting object was placed on a conveyor belt. A first light source irradiated the object with visible light having low intensity. Then, a second light source irradiated the object with high intensity, and the object was polymerized. No cracks were observed in the polymerized object upon removing it from the mold. Thus, in the '686 Patent, multiple light sources having different intensities are used to irradiate the article. The intensity of the irradiated light varies depending upon the position of the article.

Feurstein et al., U.S. Pat. No. 5,922,605 ("the '605 Patent") discloses a polymerization apparatus for light-curing objects including dental workpieces. The '605 Patent recognizes that the time for light-curing an object can be shortened when the object is also heated. Thus, the '605 Patent describes a process, whereby an object is placed in an apparatus, and a light source is switched on. The light source begins to polymerize the object. After the object has been irradiated with the light for a period of time, for example, 10 minutes, a separate and independent heat source is switched on. Heating takes place for another 10 minutes or other suitable time period. Then, the heating and light sources are switched off, and the object is cooled to end the polymerization cycle. Thus, in the '605 Patent, the heat source is used to heat the article sufficiently so that the time for curing the article is reduced.

Although the foregoing light-curing systems might be somewhat effective, it would be especially desirable to have a system, whereby an integrated lighting and heating source could be used to polymerize and cure the article. In such a system, one lighting source for irradiating the article with light and a second heating source for treating the article with heat would not be needed. Rather, the same single source would provide sufficient light and heat to polymerize the article. A system that used a single source to provide curing light and heat would be advantageous for several reasons. In such a system, the heat generated from the light source could be used to internally melt articles having a partial crystalline structure. At the same time, the light generated by the lighting source would initiate polymerization of the article. The heat would be controlled so that the article did not substantially lose its mechanical integrity or original shape, while the article was polymerized. The light would be controlled so that the article could be uniformly and fully polymerized. A system that produces a polymerized and cured article according to the following steps would be particularly desirable. A first polymerizable material would be light-cured using a lighting and heating source having a temperature within a first temperature range. Then, a second polymerizable material would be positioned on or adjacent to the first polymerized material, and the second material would be light-cured using a lighting and heating source having a temperature within a second temperature range. In such a system, the light and heat should be controlled so that the materials do not substantially change their shapes while ensuring that the materials are polymerized fully. The material must be hardened sufficiently so that it has sufficient mechanical integrity and strength. Such a system could be used advantageously to produce full and partial dentures and other dental devices. The present invention provides such a system.

SUMMARY OF THE INVENTION

The invention provides a light-curing method including the steps of: providing a light-curing apparatus having at least one integrated lighting and heating source and a curing volume. The light-curing apparatus also includes a temperature controller, which is preferably a fan. A first polymerizable material is positioned within the curing volume. The light source and temperature controller are controlled to heat the first polymerizable material to temperatures within a first temperature range. The light source and temperature controller are controlled to maintain the first polymerizable material at temperatures within the first temperature range for at least one (1) minute so that the first material is at least partially polymerized. A second polymerizable material is applied on or adjacent to the first polymerizable material within the curing volume. The light source and temperature controller are controlled to heat the second polymerizable material to temperatures within a second temperature range. The light source and temperature controller are controlled to maintain the second polymerizable shaped material at temperatures within the second temperature range for at least one (1) minute. The first temperature range has a first midpoint and the second temperature range has a second midpoint. The first midpoint temperature is at least 10° C. apart from the second midpoint temperature. The system is particularly suitable for making dental devices such as full dentures, removable partial dentures, relines of full and partial dentures, nightguards, occlusal splints, and the like.

BRIEF DESCRIPTION OF THE DRAWINGS

FIG. 1 shows a schematic diagram of a light-curing apparatus used for carrying out the method of the invention.

DETAILED DESCRIPTION OF THE PREFERRED EMBODIMENTS

The invention is now described with more particular reference to FIG. 1, which shows a light-curing apparatus (10) for use in carrying out the method of the invention. Light-curing apparatus (10) has chamber wall (12) enclosing a curing volume (14). Shaped, polymerizable material (16) is supported in curing volume (14) on turntable (18). Processor (20) controls light/heat source (22) and fan (24) by sending electrical signals through electrical conductors (26) and (28).

The invention provides a method for light-curing dental materials. The method is described herein as being used primarily to treat two polymerizable dental materials. However, it should be understood that the method refers to two dental materials for illustrative purposes only and this should not be considered restrictive. The method of this invention can be used to cure more than two polymerizable materials if needed. In FIG. 1, at least two polymerizable dental materials, independently and collectively indicated as (16), are placed in a light-curing apparatus (10) having an integrated lighting and heating source (22) for transmitting light and heat onto the materials (16). The light and heat causes the polymerizable materials (16) to be polymerized and cured. The lighting/heating source (22) preferably includes at least five incandescent bulbs. The light-curing apparatus further includes a temperature controller, which is preferably a fan (24). More preferably, the light-curing apparatus (10) includes at least one intake fan, at least one exhaust fan and at least one circulation fan. The rotation of each fan is preferably independently controlled by the processor (20).

The intensity of light from the lighting/heating source (22), which is irradiated onto the first polymerizable material (16), and rate of rotation of each fan (24) are controlled to heat the first material (16) to temperatures within a first temperature range. Then, the lighting/heating source (22) and fan (24) are controlled to maintain the first polymerizable material (16) at temperatures within the first temperature range for at least one (1) minute. In this first light-curing and heating phase, the material (16) is at least partially polymerized without substantially losing its original shape.

Then, a second polymerizable material (16) is positioned on or adjacent to the first polymerizable material (16), which is at least partially polymerized at this point, in the curing volume (14). Before the second polymerizable material (16) is placed in the curing volume (14), it is preferably heated. For example, the second polymerizable material (16) may be heated to form a molten resin, which then may be applied to the first polymerizable material (16). The intensity of light from the lighting/heating source (22), which is irradiated onto the second polymerizable material, and rate of rotation of each fan (24) are controlled to heat the second material to temperatures within a second temperature range. Then, the lighting/heating source (22) and fan (24) are controlled to maintain the second polymerizable material (16) at temperatures within the second temperature range for at least one (1) minute. In this second light-curing and heating phase, the first and second materials (16) are polymerized without substantially losing their original shapes. Significantly, the first temperature range has a first midpoint and the second temperature range has a second midpoint. The first midpoint temperature is at least 10° C. apart from the second midpoint temperature. Preferably the first midpoint temperature is at least 15° C. apart from the second midpoint temperature.

As described above, the system of this invention uses a single lighting/heating source to irradiate the article with curing light and heat. Suitable lighting/heating sources include, for example, halogen lamps, xenon lamps, and mercury lamps, provided that the intensities of the light and heat are in synchronization. Halogen lamps are preferred, because these lamps are more economically feasible. The heat generated from the light source must be sufficient to internally melt materials having a partial crystalline structure. In the system of the present invention, a temperature controller, for example, a fan (24) is used to control the heat's temperature. It is important to prevent excessive heating of the material; otherwise, the shape and dimensions of the material will substantially change. Thus, the heat energy is sufficient to causes a phase change in the material, but the heat energy is not so great so as to cause substantial deformation of the material's shape. The heat energy is not used to shorten the curing cycle as done in prior art systems; rather, it is used to internally melt the crystalline material. At the same time, the curing light is controlled so that the material is uniformly and fully polymerized. That is, the intensities of the light and heat are synchronized in the system of this invention. The levels of light energy and heat energy imparted to the material are kept in balance.

If there is no synchronization and the heat energy imparted to the material is much greater than the imparted light energy, there is excessive heating. This results in the shape of the material becoming significantly deformed. The geometry and dimensions of the material are substantially changed. On the other hand, if the curing light energy imparted to the material is much greater than the imparted heat energy, there is less internal melting of the material's crystalline structure. The internal temperature of the material is not increased sufficiently. And, the crystalline structure becomes "locked in place." As a result, there is low polymerization conversion. The material does not fully polymerized and consequently has low mechanical strength and integrity. More particularly, it there is excessive heating of the material during the curing cycle so that the material is heated to a temperature significantly greater than its glass transition temperature (Tg), the shape of the material tends to substantially change. On the other hand, if there is insufficient heating of the material, so that the material is heated to a temperature significantly less than its Tg, the material is not hardened sufficiently. In such a case, the mechanical strength of the material is weakened. If the material (device) is fixed on a supporting model, the temperature profile may need to be slightly above the Tg of the material to achieve improved strength. If the material (device) is free standing and there is no supporting model, the temperature profile may need to be slightly below the Tg of the material for improved shape stability.

In one embodiment of the invention the first temperature range is within 5° C. of the first midpoint temperature and the second temperature range is within 5° C. of the second midpoint temperature. For example, if the first midpoint temperature is 95° C., then the first temperature range extends from 90° to 100° C. A first polymerizable material (16) is placed on the turntable (18) within the curing volume (14). In one embodiment, the first polymerizable material is used to form a baseplate for a denture as described in further detail below. The first polymerizable material may be a "wax-like" polymerizable material. By "wax-like" as used herein, it is meant any material which is flowable (fluid) above 40° C. and which becomes dimensionally stable (i.e., it solidifies and is non-fluid) at a temperature of at least and below 23° C. Flowable wax-like material having a temperature in the range of 40° C. to 100° C. becomes dimensionally stable within five minutes by cooling it to an ambient temperature in the range of 0° C. to 23° C. Wax-like polymerizable materials include, for example, methacrylate (or acrylate) compounds prepared by reaction of a urethane pre-oligomer with hydroxylalkyl-methacrylate. Such wax-like polymerizable materials are described in Sun et al., U.S. Pat. No. 6,592,369, the disclosure of which is incorporated herein by reference. The lighting/heating source (22) and fan (24) of the light-curing apparatus (10) are controlled to heat the first polymerizable material (16) to temperatures within a first temperature range. The material (16) is maintained at temperatures within the first temperature range for at least one (1) minute, whereby the material (16) is partially polymerized without a substantial loss of its original shape. A preferred first temperature range has a midpoint temperature in the range of about 60° to –110° C. The time period of the first curing cycle will vary, but it is typically within the range of about 2 to about 10 minutes.

Subsequently, a second polymerizable material can be positioned on or adjacent to the first polymerizable material, which has been at least partially polymerized at this point. In one embodiment, the second polymerizable material is used to line the outer surface of the baseplate and affix the artificial teeth. The second polymerizable material can have either the same or different composition as the first polymerizable material. Preferably, the second polymerizable material has a different composition. Wax-like polymerizable materials, as described above, are used preferably as the second polymerizable material in accordance with this invention. The lighting/heating source (22) and fan (24) of the light-curing apparatus (10) are controlled to heat the second polymerizable material to temperatures within a second temperature range. The second material is maintained at temperatures within the second temperature range for at least one (1) minute, whereby the first and second materials are polymerized. Significantly, the heating of the first and second polymerizable materials is controlled during this second heating phase so that the first and second materials do not have a substantial loss of shape. A preferred second temperature range has a midpoint temperature in the range of about 90° to –150° C. The time period of the second curing cycle will vary, but it is typically within the range of about 2 to about 10 minutes.

In a preferred embodiment of the invention the curing zone or volume (14) in the light-curing apparatus (10) has a diameter of 5 inches and a height of 3 inches. The curing lamp system provides an intensity of at least 3 mW/cm$^2$ of light having wavelengths from 350-500 nm, (more preferably having wavelengths from 350-410 nm) wherein the light is substantially evenly distributed throughout the curing zone (14). The turntable (18), which holds the polymerizable material (16) preferably rotates at 3-7 revolutions per minute (rpm). The elevation of the turntable (18) is adjustable, so that the upper face of the turntable (18), is movable from the bottom plane of the curing zone (14), which is at a height of 0 inches, to a raised height of about 2 inches.

The system is particularly suitable for making dental devices such as, for example, full dentures, removable partial dentures, relines of full and partial dentures, nightguards, occlusal splints, and the like.

In one preferred embodiment, a full denture is made using the system and method of this invention. To make the denture, a dentist first takes an impression of a patient's dental anatomy using techniques well known in the art. In one customary method, a paste-like material, such as an alginate, is placed in a standard or custom-made impression tray. The dentist inserts the tray in the mouth of the patient, and the patient bites down into the tray. Separate impression trays for the upper and lower dental arches are used. The dentist removes the trays from the patient's mouth and sets them aside. The dentist typically sends the hardened impressions to a dental laboratory that will produce the denture. The dental technician, at the laboratory, prepares casts (models) of the upper and lower arches by pouring dental plaster into the hardened impressions. The plaster typically contains gypsum. The resulting plaster model has a shaped surface closely representing the patient's dental anatomy. In the laboratory, the dental technician applies a thin, smooth coating of a releasing agent (for example, silicone or alginate) to the dental model and places the coated model in a conditioning oven. Heating time and temperature will vary, but the model is typically heated to a temperature in the range of 120° to 130° F. (49° to 54° C.) for about 30 minutes.

The denture base (baseplate) is next prepared by molding a first polymerizable material over the warm model. The polymerizable resin is applied so that it fully covers the surface of the model. The resin is carefully applied to the labial/buccal and palatal/lingual surfaces on the model so as to avoid air entrapment. The resin should be applied at a uniform thickness. Using fingers and modeling instruments, the resin is applied smoothly to the model. Any excess material is trimmed away using a knife or other sharp instrument. Then, a thin layer of an air barrier coating may be applied over the entire surface of the resin-coated model. The air barrier coating helps to ensure optimum curing of all surfaces. The resin-coated model then is placed in the light-curing apparatus described above. Then, the resin-coated model is irradiated with curing light and heated to a suitable temperature. In one embodiment of a curing cycle, the temperature of the light-curing apparatus is room temperature at 0 minutes, about 75° C. at two minutes, about 100° C. at four minutes, and about 140° C. at ten minutes.

When the curing cycle has been completed, the cured baseplate and supporting model are removed from the light-curing apparatus. The baseplate/model should be allowed to cool until it reaches ambient temperature. The cured baseplate is then removed from the model. To facilitate removal of the baseplate from the model, the baseplate/model assembly may first be soaked in tap water for 5 to 15 minutes. Excess material may be trimmed from the borders of the cured baseplate. The surfaces of the baseplate should be smooth and even. Then, the dental laboratory technician applies wax occlusal rims to the baseplate and sends the baseplate to the dentist so that he can evaluate the fit of the baseplate in the patient's mouth. The dentist may adjust the wax rims for proper lip support and make occlusal and aesthetic markings (for example, smile line) on the wax rims. The dentist then returns the baseplate to the dental laboratory. The baseplate is mounted on the model and the occlusal and aesthetic markings from the baseplate are transferred to the model. While the baseplate is still on the model, the wax material is cleaned from the baseplate by rinsing with clean boiling water. After cooling, the outer surface of the baseplate is roughened-up using a bur or diamond. This will help improve bonding of the artificial teeth to the outer surface of the baseplate. Then, the entire surface of the denture baseplate is cleaned using a cleaning agent such as isopropyl or ethyl/denatured alcohol and dried with blown air. The artificial teeth are now ready to be set on the baseplate.

First, a sheet or rope of a polymerizable material, also referred to as a set-up resin, is placed onto the outer surface of the baseplate. The surface of the set-up resin is melted with an electric spatula or hot air gun just prior to tooth placement. The teeth are then pressed into the set-up resin while the resin is in a softened condition. Then, a molten polymerizable material, also referred to as molten contour resin, which has been prepared previously by placing the resin in a melting pot set at a high temperature, for example, at about 189° F., is applied so that it flows around the embedded artificial teeth. The contour resin should flow between the embedded teeth smoothly and evenly, because, once the resin hardened, it will hold the teeth in position. As the contour resin flows around the embedded teeth, it covers the set-up resin and any exposed baseplate. The uncured denture is now ready to be sent to the dentist so that he or she can place it in a patient's mouth as a "try in." The dental laboratory sends the uncured denture to the dentist. Due to the light-curing nature of the materials, the denture is sent in a light-safe bag.

The dentist seats the denture in the patient's mouth and evaluates its fit. This procedure is commonly referred to as a "try in." It may be necessary to make adjustments to the baseplate and embedded teeth according to the dental anatomy of the patient. The denture should be fitted so that it conforms tightly to the contours of the patient's oral cavity and there is good occlusion. Since the denture is uncured and has an extended working time, the dentist can make some minor chairside adjustments. Then, the denture device is sent back to the dental laboratory so that the final denture device can be prepared. If needed, the laboratory technician can reposition the anterior and posterior teeth and make other major adjustments.

At the laboratory, the denture is placed back on the model (a new model may be prepared if needed), and an air barrier coating is applied so that it covers all external resin surfaces and embedded teeth. The denture and supporting model are placed in a conditioning oven and heated at 130° F. for at least one hour. The denture/model is removed from the conditioning oven and a model releasing agent is applied to the flange areas of the denture. In one embodiment, the denture is sealed to the model by applying a sealing gel to the borders of the denture. Next, the denture/model is placed in the light-curing apparatus described above. The denture/model is heated to a suitable temperature and light-cured. In one embodiment, the temperature of the light-curing apparatus is about 50° C. at 0 minutes, about 85° C. at two minutes, about 95° C. at four minutes, and about 105° C. at ten minutes.

After the light-curing/heating cycle has been completed, the denture/model is removed and allowed to cool until the denture reaches ambient temperature. Then, the denture is separated from the model. The cured sealing gel is removed from the denture and the air barrier coating is washed away with water and a soft brush. Finally, the denture is finished and polished using conventional techniques. Workers skilled in the art will appreciate that various modifications and additional steps can be made to above-described method for making denture devices. The foregoing method is provided for illustration purposes only and should not be considered restrictive.

The invention is illustrated by the following examples, which are not intended to be limiting. Exemplary compositions, which may be used as the light-curable polymerizable materials, are described in the following Examples 1-6. Exemplary dental devices, which may be made from the light-curable polymerizable materials, are described in the following Examples 7-9.

EXAMPLES

Example 1

Preparation of Oligomer

A reactor was charged with 1176 grams of trimethyl-1,6-diisocyanato-hexane (5.59 mol) and 1064 grams of bisphenol A propoxylate (3.09 mol) under dry nitrogen flow and heated to about 65° C. under a positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes. To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

Example 2

Preparation of Monomer

A reaction flask was charged with 700 grams of 1,6-diisocyanatohexane and heated to about 70° C. under a positive nitrogen pressure. To this reactor were added 1027 grams of 2-hydroxyethyl methacrylate, 0.75 gram of catalyst dibutyltin dilaurate and 4.5 grams of butylated hydroxy toluene (BHT). The addition was slow and under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

Example 3

Preparation of Polymerizable Denture Contour Material

A wax-like polymerizable dental material was prepared by stirring at 85° C., a liquid mixture of 63.0 grams of oligomer made the procedure of Example 1 and 37.0 grams of compound of Example 2, 0.35 gram of 2,4,6-trimethylbenzoyldiphenylphosphine oxide, (Lucirin TPO made by BASF), 0.5 gram of solution containing 8.3% camphorquinone (CQ), 25% ethyl 4-dimethylaminobenzoate (EDAB) and 66.7% 1,6-hexanediol dimethacrylate (HDDMA).

Example 4

Preparation of Polymerizable Denture Base Plate (or Reline) Material

A light curable polymerizable material was prepared by stirring at 85° C., a liquid of 98.0 grams of TBDMA oligomer of Example 1, 0.35 gram of 2,4,6-trimethylbenzoyidiphenylphosphine oxide, (Lucirin TPO made by BASF), 1.5 gram of solution containing 8.3% camphorquinone (CQ), 25% ethyl 4-dimethylaminobenzoate (EDAB) and 66.7% 1,6-hexanediol dimethacrylate (HDDMA), 0.1 gram of red acetate fibers and 0.05 gram of pigment.

Example 5

Preparation of Polymerizable Wax-Like Denture Contour Material

A light curable wax-like polymerizable dental material was prepared by stirring at 85° C., a liquid mixture of 50.5 grams of oligomer of Example 1, 45.0 grams of monomer of Example 2, and 4.0 grams of stearyl acrylate from Sartomer. To this mixture were added 0.35 gram of 2,4,6-trimethylbenzoyidiphenylphosphine oxide (Lucirin TPO), 0.1 gram of red acetate fibers and 0.05 gram of pigment concentrates. The polymerizable wax-like material formed becomes flowable at 65 to 68° C.

Example 6

Preparation of Polymerizable Denture Set-Up Material

A light curable polymerizable material was prepared by stirring at 85° C., a liquid mixture of 84.5 grams of oligomer of Example 1 and 15.0 grams of monomer of Example 2. To this mixture, 0.35 gram of 2,4,6-trimethylbenzoyldiphenylphosphine oxide (Lucirin TPO), 0.1 gram of red acetate fibers and 0.05 gram of pigment were added.

Example 7

Preparation of a Denture without Forming a Mold Cavity of a Denture Base

A plaster cast of a patient's mouth is coated with a release agent (e.g., Al-Cote® and Isolant® sold by Dentsply International Inc. or Teflon® solution such as Krytox® from DuPont) and heated to 55° C. in an incubator. An arch-shaped baseplate resin containing 14 grams of the product of Example 4 is applied and shaped onto the warm cast. The resin is shaped and flowed to fully cover the cast, using finger pressure and trimming to form a baseplate. The baseplate is cured for 10 minutes in the visible light-curing unit. The temperature of the device is at room temperature at 0 minute, around 75° C. at 2 minutes, 100° C. at 4 minutes, and 140° C. at 10 minutes. A sufficient quantity of the product of Example 6 is formed into a rope. The rope is applied to the baseplate. Then artificial teeth are pressed into the rope with the thickness of the rope adapted to adequately cover the appropriate surfaces of the teeth to provide support. Melted product of Example 5 from an 87° C. wax pot is applied by using an electric spatula between the teeth and the baseplate to fully embed teeth and to flow into fissures between teeth and to smooth the outer surface of the denture. Hot air from a small nozzle hot air gun may also be applied to let the product of Example 5 flow into fissures between teeth and smooth the outer surface of the denture. The lingual and buccal surfaces of the denture are contoured, trimmed and carved using a spatula. The denture is placed in a patient's mouth for try-in at a dental office and tooth positions are adjusted. The denture back is fitted to the cast and the TRIAD Air Barrier Coating is painted on the denture. The denture is placed into conditioning oven at 55° C. for at least 1 hour. A model release agent (MRA) sold by Dentsply International Inc. is applied to around the border of denture and the cast immediately. A strip of Triad gel is applied on surface between the border and the cast and cured in a visible light-curing unit for 10 minutes. The temperature of the device is 50° C. at 0 minutes, around 85° C. at 2 minutes, 95° C. at 4 minutes, and 105° C. at 10 minutes. When cured, the denture is washed with water to remove all traces of Air Barrier Coating. The denture is then finished and polished.

Example 8

Preparation of a Partial Denture Without Forming a Mold Cavity (Investment) of a Denture Base A removable partial denture framework is fabricated. A separating medium is applied to a gypsum cast of the patient's dentition. A sufficient quantity of the product of Example 4 is applied onto the edentulous areas of the cast and adapted with finger pressure or appropriate instruments. Excess material is trimmed with a hot spatula. A sufficient quantity of the product of Example 4 is adapted into the tissue side finish line of the partial denture framework. The framework is seated on the cast firmly, embedding the uncured material of Example 4. All rests and tissue stops are varnished as correctly positioned on the cast, indicating that the framework is fully seated. Excess material is removed and these baseplate areas are cured in the visible light-curing unit. The temperature of the device is at room temperature at 0 minute, around 50° C. at 2 minutes, 80° C. at 4 minutes and 90° C. at 10 minutes. A rope of the product of Example 6 is adapted onto the precured baseplate/edentulous areas. The rope has a thickness sufficient to cover the ridge lap surfaces of the teeth to provide support for the teeth and to seat the teeth, which are then set up in the rope. A portion of the product of Example 5 is applied between the teeth and the baseplate. A small nozzle hot air gun is used to melt the product of Example 5 so that it flows into the fissures between teeth as the outer surface smoothes. The lingual and buccal surfaces of the edentulous areas are contoured, trimmed and carved using an electric hot spatula, sharp tools and hot air gun. The partial denture wax-up is removed from the cast for try-in. The denture is placed in a patient's mouth for try-in at a dental office and tooth positions adjusted if needed. The partial denture is fitted to a modified cast (reduced soft tissue heights of contour). TRAID Air Barrier Coating is painted onto the denture. Then a mold release agent (MRA) sold by Dentsply International, Inc. is applied around the posterior teeth and supporting resin. A strip of triad gel is applied between teeth and on the surface of the supporting resin to form a continuous circle. The denture is then cured in the visible light-curing unit for 10 minutes. The temperature of the device is at room temperature at 0 minutes, around 80° C. at 2 minutes, 95° C. at 4 minutes, and 105° C. at 10 minutes. When cured, the partial denture is washed with water to remove all traces of Air Barrier Coating. The partial denture is then finished and polished.

Example 9

Preparation of a Night Guard Without Forming a Mold Cavity of a Night Guard

A plaster cast of a patient's teeth is coated with a release agent. 20 grams of the product composition of Example 3 is applied over the release agent and warmed to 50° C. in an oven. The composition is shaped using finger pressure and trimming to form a night guard which hardens when cooling to room temperature. The surfaces of the night guard are contoured, trimmed and carved using an electric hot spatula and hot air gun. After the night guard is examined and adjusted to fit articulator, the night guard is fitted to the cast and a TRAID Air Barrier Coating is painted on the denture and cured for 10 minutes. The temperature of the device is at room temperature at 0 minutes, around 95° C. at 2 minutes, 100° C. at 4 minutes, and 110° C. at 10 minutes. The clear night guard is then washed with water to remove all traces of Air Barrier Coating. The night guard is then finished and polished.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method for light-curing polymerizable materials to form a dental device, comprising the steps of:
    providing a light-curing apparatus having a least one light source and a curing volume;
    positioning a first polymerizable material within said curing volume;
    heating said first polymerizable material to a temperature within a first temperature range;
    maintaining said first polymerizable material at the temperature within said first temperature range for at least one minute;
    positioning a second polymerizable material on said first polymerizable material that has been at least partially polymerized, within said curing volume;
    heating said second polymerizable material to a temperature within a second temperature range; and
    maintaining said second polymerizable material at the temperature within said second temperature range for at least one minute, said first temperature range having a first midpoint and second temperature range having a second midpoint said first midpoint temperature being at least 10° C. apart from said second midpoint temperature;
    wherein the intensity of light energy and heat energy imparted on the first polymerizable material is controlled to cure the first polymerizable material while not causing a substantial deformation of shape; and
    wherein the intensity of light energy and heat energy imparted on the second polymerizable material is controlled to cure the second polymerizable material while not causing a substantial deformation of shape.

2. The method of claim 1, wherein said first temperature range is within 5° C. of said first midpoint temperature and said second temperature range is within 5° C. of said second midpoint temperature.

3. The method of claim 1, wherein said first midpoint temperature of said first temperature range is at least 15° C. from said second midpoint temperature of said second temperature range.

4. The method of claim 1, wherein said first temperature range has a midpoint temperature between 100° C. and 110° C.

5. The method of claim 1, wherein said first temperature range has a midpoint temperature between 120° C. and 150° C.

6. The method of claim 1, wherein the second polymerizable material is a wax-like polymerizable material.

7. The method of claim 1, wherein the dental device is selected from the group consisting of full dentures, partial dentures, denture relines, nightguards, and occlusal splints.

8. The method of claim 7, wherein the dental device is a full denture.

9. The method of claim 7, wherein the dental device is a partial denture.

10. The method of claim 1, wherein the light-curing apparatus further comprises a processor, said processor being connected by an electrical conductor to said light source.

11. The method of claim 1, wherein the light-curing apparatus further includes at least one fan.

12. The method of claim 11, wherein the light-curing apparatus further comprises a processor, said processor being connected by an electrical conductor to said at least one fan.

13. The method of claim 1, wherein the composition of the first polymerizable material is different from the composition of the second polymerizable material.

14. The method of claim 1, wherein the positioning step of the first polymerizable material, the first polymerizable material is positioned about a turntable.

15. The method of claim 14, wherein the elevation of the turntable is adjustable, so that an upper face of the turntable, is movable from the bottom plane of the curing volume.

16. The method of claim 1, wherein the at least one light source provides an intensity of at least 3 mW/cm$^2$ of light having wavelengths from 350-500 nm, so that the light is substantially evenly distributed throughout the curing volume.

17. The method of claim 1, wherein:
    (i) said first temperature range is within 5° C. of said first midpoint temperature and said second temperature range is within 5° C. of said second midpoint temperature;
    (ii) said first midpoint temperature of said first temperature range is at least 15° C. from said second midpoint temperature of said second temperature range;
    (iii) the second polymerizable material is a wax-like polymerizable material;
    (iv) the composition of the first polymerizable material is different from the composition of the second polymerizable material;
    (v) the light-curing apparatus further comprises at least one fan; and
    (vi) the positioning step of the first polymerizable material, the first polymerizable material is positioned about a turntable.

18. The method of claim 17, wherein the at least one light source provides an intensity of at least 3 mW/cm$^2$ of light having wavelengths from 350-500 nm, so that the light is substantially evenly distributed throughout the curing volume.

19. The method of claim 17, wherein:
    (i) the light-curing apparatus further comprises a processor, said processor being connected by an electrical conductor to said light source; and
    (ii) the processor being connected by an electrical conductor to said at least one fan.

20. The method of claim 19, wherein the at least one light source includes at least five incandescent bulbs and the at least one fan includes at least one intake fan, at least one exhaust fan and at least one circulation fan.

* * * * *